US00PP27905P3

(12) United States Plant Patent

Klemm et al.

(10) Patent No.: US PP27,905 P3

(45) Date of Patent: Apr. 18, 2017

(54) *DIANTHUS* PLANT NAMED 'KLEDG14178'

(50) Latin Name: ***Dianthus* sp.**
Varietal Denomination: KLEDG14178

(71) Applicant: Klemm+Sohn GmbH & Co. KG, Stuttgart (DE)

(72) Inventors: Nils Klemm, Stuttgart (DE); Martin Glawe, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 67 days.

(21) Appl. No.: 14/545,531

(22) Filed: May 18, 2015

(65) Prior Publication Data

US 2016/0014949 P1 Jan. 14, 2016

Related U.S. Application Data

(60) Provisional application No. 61/998,888, filed on Jul. 10, 2014.

(51) Int. Cl.
*A01H 5/02* (2006.01)

(52) U.S. Cl.
USPC ..... Plt./273

(58) Field of Classification Search
USPC ..... Plt./272, 273, 278
See application file for complete search history.

*Primary Examiner* — Anne Grunberg

(74) *Attorney, Agent, or Firm* — James M. Weatherly; Barbara Campbell; Cochran Freund & Young, LLC

(57) ABSTRACT

A new *dianthus* plant named 'KLEDG14178' particularly distinguished by purple-red flowers with a dark red center and small, dark blue-green foliage, is disclosed.

1 Drawing Sheet

Genus and species: *Dianthus* sp.
Variety denomination: 'KLEDG14178'.

BACKGROUND

The present invention comprises a new and distinct variety of *Dianthus*, botanically known as *Dianthus* sp. and hereinafter referred to by the variety name 'KLEDG14178'. 'KLEDG14178' originated from a branch mutation found on the proprietary *dianthus* line 'DSU 2011 0033' (unpatented).

In June 2011 'KLEDG14178' was discovered as a mutation from the proprietary dianthus line 'DSU 2011 0033' in Stuttgart, Germany. 'KLEDG14178' was first vegetatively propagated in June 2011 in Stuttgart, Germany by vegetative stem cuttings. 'KLEDG14178' was found to reproduce true to type in successive generations of asexual propagation via vegetative stem cuttings in Stuttgart, Germany.

SUMMARY

The following are the most outstanding and distinguishing characteristics of this new variety when grown under normal horticultural practices in Stuttgart, Germany.

1. Purple-red flowers with a dark red center; and
2. Small, dark blue-green foliage.

DESCRIPTION OF THE PHOTOGRAPH

These new *Dianthus* plant is illustrated by the accompanying photograph, which shows the overall plant habit of the variety 'KLEDG14178' grown in a pot. The photograph is of a 10 to 12 week old plant in Stuttgart, Germany grown under greenhouse conditions in May 2013.

The colors shown are as true as can be reasonably obtained by conventional photographic procedures.

DESCRIPTION OF THE NEW VARIETY

The following detailed descriptions set forth the distinctive characteristics of 'KLEDG14178'. The data which define these characteristics were collected from asexual reproductions carried out in Stuttgart, Germany. Data was collected on four month old plants grown in a glass greenhouse in Stuttgart, Germany in March, 2014. Color references are to The R.H.S. Colour Chart of The Royal Horticultural Society of London (R.H.S.), 5$^{th}$ edition.

Classification:
- *Family.*—Caryophyllaceae.
- *Species.*—*Dianthus* sp.
- *Common name.*—Garden carnation.
- *Type.*—Spray type carnation.

Parentage: Mutation from the proprietary *dianthus* 'DSU 2011 0033'.

Propagation:
- *Type.*—Vegetative stem cuttings.
- *Time to produce a rooted young plant.*—About 20 days.
- *Root description.*—Small, white, well-branched.
- *Rooting habit.*—Lanceolate.

Plant description:
- *Plant form.*—Potted and garden plant, bushy.
- *Plant height.*—10.0 cm.
- *Plant diameter or spread.*—18.0 cm.

Lateral branches:
- *Stem.*—Solid.
- *Length.*—6.0 cm.
- *Diameter.*—1.5 cm.
- *Number of internodes per stem.*—3 to 4.
- *Internode length.*—0.6 cm.
- *Node length.*—0.3 cm.
- *Node diameter.*—0.3 cm.
- *Texture.*—Smooth.
- *Color.*—RHS 137B.

Foliage description:
- *Arrangement.*—Opposite.
- *Length.*—5.0 cm.
- *Width.*—0.2 cm.

*Shape*.—Lanceolate.
*Apex*.—Acute.
*Base*.—Obtuse.
*Margin*.—Entire.
*Texture*.—Upper and lower surfaces: Smooth.
*Color*.—Immature and mature leaves: Upper surface: RHS 137B. Lower surface: RHS 137C.
*Venation pattern*.—Parallel.
*Venation*.—RHS 137D.

Flower description:
*Flower type and habit*.—Single, round.
*Flower position*.—Slightly above the foliage.
*Fragrance*.—Absent.
*Natural flowering season*.—Spring to fall.
*Flower longevity*.—6 to 8 days.
*Number of flowers per spray*.—3 to 4.
*Flower buds*.—Length: 1.8 cm. Diameter: 0.5 cm. Shape: Cylindrical. Color: RHS 137C. Extrusion of the styles at bud stage: Absent.
*Corolla*.—Quantity of petals/arrangement: 5, whorled. Corolla height: 0.5 cm. Petal length: 3.0 cm. Petal width: 1.4 cm. Petal shape: V-shaped. Petal apex: Obtuse. Petal base: Cuspidate. Petal margin: Serrate, depth is medium. Petal texture: Upper and lower surfaces: Smooth. Petal color: Immature: Upper surface: Main color is RHS 61B and the secondary color in the eye is RHS 59A. Lower surface: RHS 61C. Mature: Upper surface: Main color is RHS 61B and the secondary color in the eye is RHS 59B. Lower surface: RHS 60C. Calyx: Quantity of sepals/arrangement: 5, single. Calyx height: 2.0 cm. Calyx diameter, at the apex: 0.5 cm. Shape: Campanulate. Sepal apex shape: Acute. Sepal texture: Upper and lower surfaces: Smooth. Sepal color: Upper surface: RHS 137C. Lower surface: RHS 137D. Epicalyx: Position of the outer lobes in relation to the calyx: Adpressed. Apex shape of inner and outer lobes: Acute. Length: 0.7 cm.

Peduncles:
*Length*.—6.0 cm.
*Diameter*.—1.0 cm.
*Strength*.—Moderate.
*Texture*.—Smooth.
*Color*.—RHS 136B.

Reproductive organs:
*Stamens*.—Quantity: Greater than 5. Filament length: 1.0 cm. Filament color: RHS 75B. Anther length: 0.15 cm. Anther diameter: 0.08 cm. Anther color: RHS 91D. Pollen amount: Sparse.
*Pistils*.—Quantity: 1. Pistil length: 0.8 cm. Style length: 0.1 cm. Style color: RHS 76D. Style shoulder: Absent. Stigma shape: Filamentous. Stigma color: RHS 72A. Ovary size: 0.4 cm. Ovary shape: Ovate. Ovary color: RHS 139D. Ovary texture: Smooth. Fruits/seeds: None observed.

Disease and insect/pest resistance: No special observations were made.

COMPARISON WITH PARENTAL LINE AND KNOWN VARIETY

When 'KLEDG14178' is compared to the parental line, the following differences are noted in Table 1:

TABLE 1

Comparison with Parental Line

| Trait | Variety 'KLEDG14178' | Female parent 'DSU 2011 0033' |
|---|---|---|
| Flower color | Purple-Red with a dark red center | Dark purple with dark center |

When 'KLEDG14178' is compared to the commercial line 'Kahori' (patent status unknown), the following differences are noted in Table 2:

TABLE 2

Comparison with Similar Variety

| Trait | Variety 'KLEDG14178' | Commercial line 'Kahori' |
|---|---|---|
| Flower color | Purple-red with a dark red center | Purple and blue |
| Color of foliage | Dark green-blue | Green |
| Size of leaves | Small | Medium |

We claim:

1. A new and distinct variety of *Dianthus* plant named 'KLEDG14178' as illustrated and described herein.

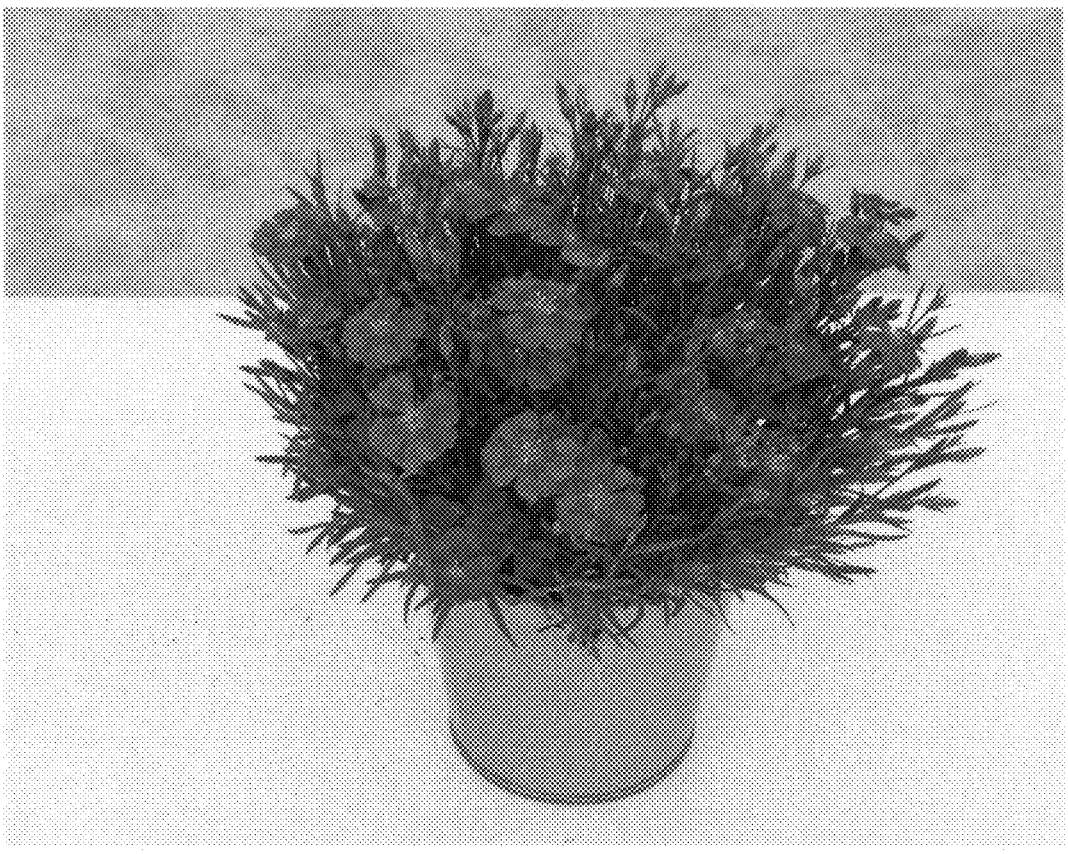

* * * * *